United States Patent [19]
Collins, Jr.

[11] Patent Number: 5,645,423
[45] Date of Patent: Jul. 8, 1997

[54] MANDIBULAR ADVANCEMENT APPLIANCE

[76] Inventor: John A. Collins, Jr., 1116 Mishawaka Ave., South Bend, Ind. 46615

[21] Appl. No.: 258,047

[22] Filed: Jun. 10, 1994

[51] Int. Cl.$^6$ .................................................. A61C 3/00
[52] U.S. Cl. .............................. 433/21; 433/18; 433/19
[58] Field of Search ............................. 433/18, 19, 20, 433/21

[56] References Cited

U.S. PATENT DOCUMENTS

| | | | |
|---|---|---|---|
| 4,197,643 | 4/1980 | Burstone et al. | 433/20 |
| 4,239,487 | 12/1980 | Murdock | 433/7 |
| 4,424,032 | 1/1984 | Howe | 433/19 |
| 4,433,956 | 2/1984 | Witzig | 433/7 |
| 4,609,349 | 9/1986 | Cain | 433/18 |
| 4,618,324 | 10/1986 | Nord | 433/19 |
| 4,619,609 | 10/1986 | Clark | 433/6 |
| 4,708,646 | 11/1987 | Jasper | 433/19 |
| 5,066,226 | 11/1991 | Summer | 433/19 |
| 5,246,366 | 9/1993 | Tracey | 433/21 |
| 5,266,028 | 11/1993 | Adkisson | 433/18 |
| 5,314,331 | 5/1994 | Brosius et al. | 433/21 |

OTHER PUBLICATIONS

Advertising Brochure for CorMar, Inc. Spring Coil Bushing from AOA, undated.
Advertising Brochure for the Jasper Jumper Appliances from AOA, undated.
Advertising for "Fixed Bionator" appliance from Ohlendorf Company, dated Jun. 1989.
Advertising Brochure for the Herbst appliances from AOA, undated.
Advertising for modified Herbst appliance from TP Orthodontics, Inc., 1992.
"Physiologic Principles of Functional Appliances," Thomas M. Graber, 1985.
Advertising Brochure for ORMCO Bite Jumping Appliance--Herbst Therapy, 1992.
Advertisement for "MALU–Mobee lock" system, Saga Dental.
Advertisement for Herbst IV Appliance, Journal of Clinical Orthodontics, May 1995.
Advertisement for Herbst Appliance Lab Services for Specialty Appliances, Journal of Clinical Orthodontics, May 1995.
Carlos Martins Coelho Filho, DDS, "Mandibular Protraction Appliances for Class II Treatment," Journal of Clinical Orthodontics, May 1995.

*Primary Examiner*—Cary E. O'Connor
*Attorney, Agent, or Firm*—Kenyon & Kenyon

[57] ABSTRACT

An orthodontic appliance which may be used to advance the mandible comprising a single element Z-shaped body including a central straight segment, a pair of oppositely curved segments disposed at opposite ends of the central straight segment, and a pair oppositely directed arms each extending from one of the oppositely curved segments. The opposing arms may be affixed to opposing upper and lower teeth on one side of the dental arch.

14 Claims, 2 Drawing Sheets

MANDIBULAR ADVANCEMENT APPLIANCE

FIELD OF INVENTION

The present invention is directed to an orthodontic appliance for use in interarch correction, and more particularly to a mandibular advancement appliance which may be used for fixed or removable applications.

BACKGROUND OF THE INVENTION

Various methods of orthodontic treatment have been used to effect advancement of the mandible. The methods can be broken down into two categories: those using removable appliances and those using fixed appliances.

Removable appliances are often popular with patients due to controllable and limited wear time while also includes the risks associated with failure of patient compliance. A patient's inability or unwillingness to wear an appliance for the prescribed period of time may lengthen treatment time or compromise the results achieved. Further, orthodontists often disfavor the use of removable appliances because of a patient's failure to cooperate or because the continuous removal and replacement of an appliance necessitates constant adjustment. Fixed appliances, though often popular among orthodontists because of reduced treatment time and better results, are often disfavored by patients. This is particularly true of the prior art fixed mandibular advancement devices. They are generally anchored to the teeth in the upper first molar buccal area and lower first bicuspid or cuspid buccal area with bulky connecting arms designed for advancement of the mandible. Such bulky appliances are not aesthetically pleasing and in some cases cause considerable discomfort. This may lead to patient rejection or non-acceptance of the appliance.

One prior art mandibular advancement device is the Herbst appliance. Briefly, the Herbst appliance and its modified versions include a central positioning rod operatively disposed between the upper and lower dental arches and anchored at opposite ends to bands or other framework on the teeth. The appliance is designed to advance the mandible or effect other jaw movements. The central positioning rod is relatively bulky to provide structural integrity. The overall device is made more bulky due to the connecting arms designed to secure the central positioning rod at opposing ends to the bands on the teeth. The connecting arms secure the central rod in place and allow hinged movement for opening and closing of the jaw. Each connecting arm comprises a separate securing element, such as a screw, to attach the central positioning rod to bands on the teeth. The screw is inserted through an eyelet in the rod and affixed to the band. The screw, thus secures the rod in place and also allows pivoting of the rod when the jaw is opened and closed. This device is bulky, is not aesthetically pleasing and is not comfortable to wear.

Another device used for effecting jaw movements is known as the Jasper Jumper and is essentially described in U.S. Pat. No. 4,708,646. The appliance includes a central positioning spring which is operatively connected at its opposing ends to the opposing dental arches. The device is affixed to bands or brackets on a patient's teeth by separate attachment components such as hook and eyelet means. The spring creates a continuous force, and the attachment components additionally allow for the opening and closing of a patient's jaw. This device includes several separate pieces and is also bulky within a patient's mouth creating patient discomfort.

SUMMARY OF THE INVENTION

In view of the shortcomings and disadvantages associated with the prior mandibular advancement devices, it is an object of the present invention to provide an orthodontic appliance which can be used in either removable or fixed applications and which would be compatible with most appliance systems.

It is another object of the present invention to provide an orthodontic appliance which corrects a plurality of jaw misconfigurations with reduced treatment time.

It is a further object of the present invention to provide an orthodontic appliance which has a unique anchorage system to allow for improved range of motion of the mandible and which is comfortable to wear.

It is a further object of the present invention to provide a mandibular advancement appliance which is durable, but which does not include the bulk normally associated with such devices.

It is a further object of the present invention to provide for an orthodontic appliance which effects jaw movements and which simultaneously provides superior comfort and aesthetics.

Briefly, the present invention provides for an orthodontic appliance which may be used to advance the mandible comprising a single element Z-shaped body including a central straight segment, a pair of oppositely curved segments disposed at opposite ends of the central straight segment, and a pair oppositely directed arms each extending from one of the oppositely curved segments. The opposing arms may be affixed to opposing upper and lower teeth on one side of the dental arch.

Other objectives and advantages will become apparent upon reading the detailed description which follows.

DETAILED DESCRIPTION

Figure 2:
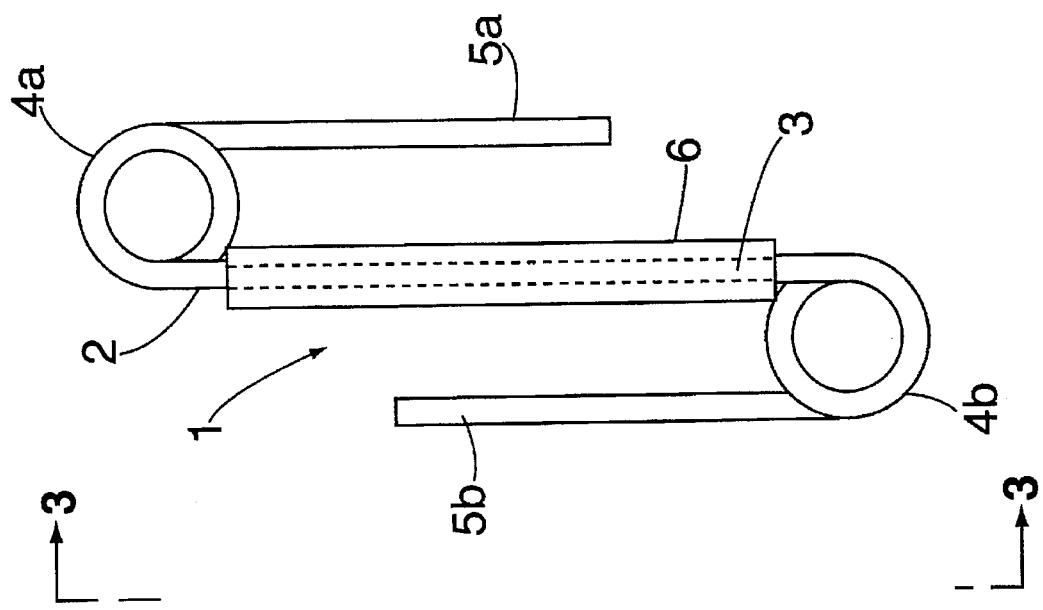
FIG. 2 is a plan view of the orthodontic appliance of the present invention.
Figure 1:
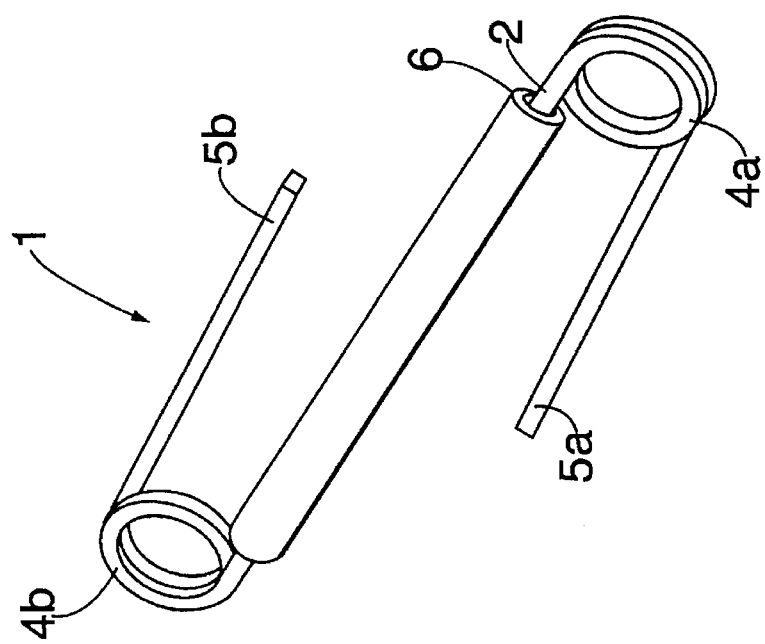
FIG. 1 is a perspective view of the orthodontic appliance of the present invention.
Figure 3:
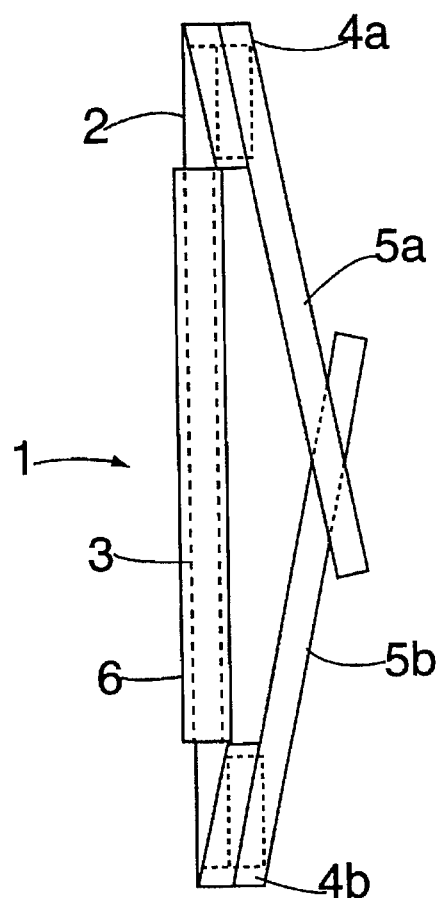
FIG. 3 is a view of the appliance of FIG. 2 cut along line 3—3.

Referring to the drawings, FIGS. 1 through 3 illustrate an orthodontic appliance constructed in accordance with the present invention. Generally, the appliance 1 may be constructed from a wire 2, which may be of any suitable material, such as stainless steel or beta titanium, preferably stainless steel and more preferably a superelastic nickel titanium wire. The appliance 1 is fabricated to include a central shaft 3 and two double helical loops 4a and 4b and two articulation arms 5a and 5b. The appliance may additionally include a sheath 6. The sheath 6 provides support to shaft 3 to prevent deformation of the shaft 3 under the forces resulting when the appliance 1 is in use. Preferably, sheath 6 is made from stainless steel or a rubberized plastic.

The appliance 1 may be affixed to a patient's upper and lower dental arches to effect advancement of the mandible or to effect distalization of molars. Preferably, the appliances is affixed to a patient's opposing upper and lower first molars.

Figure 4:
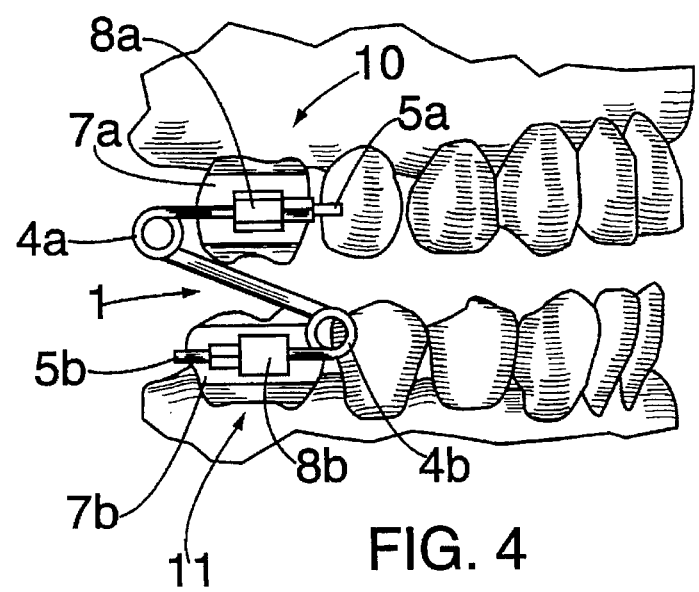
FIG. 4 is a view of the orthodontic appliance of the present invention in use inside the mouth of a patient as attached to the buccal surface of bands affixed to a patient's first molars.

FIG. 4 represents the orthodontic appliance of the present invention in place inside a patient's mouth. Metallic bands 7a and 7b are seated around upper first molar 10 and lower first molar 11. The bands may be affixed to the teeth by any conventional means such as with cement glue. The bands 7a and 7b have attachment means such as metallic tubes 8a and 8b affixed thereto. Where a tube is employed, the tube opening (not shown) may be round or rectangular in cross section, but is large enough for the passage of articulation arms 5a or 5b of the appliance of the present invention.

The orthodontic appliance is secured in place by inserting opposing articulation arms 5a and 5b through tubes 8a and 8b. The tube 8a affixed to the band on the upper first molar 10 receives a first arm 5a of the orthodontic appliance initially through the distal opening of the tube, such that when the appliance 1 is in place, the free tip of the first arm 5a points forward in the patient's mouth and the first double helical loop 4a is directed distally. Alternately, the tube 8b affixed to the band on the lower first molar 11 receives a second arm 5b initially through the mesial opening of the tube such that when the appliance 1 is in place, the free tip of the second arm 5b points in the distal direction in the patient's mouth and the second double 4b helical loop is directed forward in the patient's mouth. The arms 5a and 5b are secured in place by means of metallic crimpable or adjustable stops 9. Other means of securing arms 5a and 5b may be employed.

In place on the buccal surface of opposing first molars, the double helical loops are positioned to allow clearance upon jaw closure, while at the same time securing the appliance close to the buccal surface of the teeth to prevent patient discomfort in the cheek area.

In use, the appliance of the present invention creates a light continuous force which effects desired movement of the teeth. The device may be used for advancement of the mandible and/or for distalization of molars. The double helical loops allow for normal jaw movement while speaking or eating and thus provide for patient comfort.

The unique single body construction of the device fabricated from a single wire with the double helical loops provides for ease of insertion and removal and additionally eliminates the bulk associated with prior art devices. The appliance thus provides an improvement in patient comfort aesthetics and compliance, while shortening treatment time. The single body construction also provides for improved dental hygiene accessibility and allows for easy patient maintenance.

The appliance may be used in conjunction with a wide variety of appliance systems in various phases of treatment and may be custom designed for fixed or removable applications.

In the foregoing specification, the present invention has been described with respect to specific embodiments. These serve as examples to illustrate the invention rather than limit its scope. Modifications may be made without departing from the broader teachings and scope of the invention.

What is claimed is:

1. An orthodontic appliance for interarch correction, comprising:

a wire body including:

a central straight segment with a first end and a second end;

a first double helical loop curved segment contiguous to the first end of the central straight segment; and a first arm contiguous to the first curved segment and extending in a first direction;

a second double helical loop curved segment of opposite curvature relative to the first curved segment and contiguous to the second end of the central straight segment; and a second arm contiguous to the second curved segment and extending in a second direction generally opposite the first direction.

2. The orthodontic appliance of claim 1, wherein the wire body is made from a nickel titanium wire.

3. The orthodontic appliance of claim 1, wherein the wire body is made from beta titanium.

4. The orthodontic appliance of claim 1, further comprising a supporting sleeve disposed about the central straight segment.

5. A mandibular advancement appliance comprising:

a single element z-shaped body which includes a central straight segment, a pair of oppositely curved segments disposed at opposite ends of the central straight segment, and a pair of oppositely directed arms means, each extending from one of the oppositely curved segments, for attachment to teeth on opposing jaws on one side of a patient's dental arch.

6. The mandibular advancement appliance of claim 5, wherein the curved segments are double helical loops.

7. The mandibular advancement appliance of claim 5, wherein the single element Z-shaped body is made from a nickel titanium wire.

8. The mandibular advancement appliance of claim 5, wherein the single element z-shaped body is made from beta titanium.

9. The mandibular advancement appliance of claim 5, further comprising a supporting sleeve disposed about the central straight segment.

10. A mandibular advancement assembly, comprising:

attachment means adapted to be affixed to each of a pair of opposing upper and lower teeth on one side of a patient's dental arch;

an orthodontic appliance which is generally z-shaped and includes a central straight segment, a pair of oppositely curved segments disposed at opposite ends of the central straight segment, and a pair of oppositely directed arms each extending distally from one of the oppositely directed curved segments, the arms being each adapted to be secured by the attachment means to the pair of opposing upper and lower teeth.

11. The mandibular advancement assembly of claim 10, wherein the attachment means are adapted to be affixed to the patient's upper and lower first molars on one side of the dental arch.

12. The mandibular advancement assembly of claim 10, wherein the curved segments are double helical loops.

13. The mandibular advancement assembly of claim 10, wherein the orthodontic appliance is made from a nickel titanium wire.

14. The mandibular advancement assembly of claim 10, further comprising a supporting sleeve disposed about the central straight segment.

* * * * *